(12) United States Patent
Rapaka et al.

(10) Patent No.: US 10,296,809 B2
(45) Date of Patent: May 21, 2019

(54) METHOD AND SYSTEM FOR FAST PATIENT-SPECIFIC CARDIAC ELECTROPHYSIOLOGY SIMULATIONS FOR THERAPY PLANNING AND GUIDANCE

(71) Applicants: Saikiran Rapaka, Eagleville, PA (US); Tommaso Mansi, Westfield, NJ (US); Bogdan Georgescu, Plainsboro, NJ (US); Ali Kamen, Skillman, NJ (US); Dorin Comaniciu, Princeton Junction, NJ (US)

(72) Inventors: Saikiran Rapaka, Eagleville, PA (US); Tommaso Mansi, Westfield, NJ (US); Bogdan Georgescu, Plainsboro, NJ (US); Ali Kamen, Skillman, NJ (US); Dorin Comaniciu, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 1506 days.

(21) Appl. No.: 13/780,230

(22) Filed: Feb. 28, 2013

(65) Prior Publication Data

US 2013/0226542 A1 Aug. 29, 2013

Related U.S. Application Data

(60) Provisional application No. 61/604,132, filed on Feb. 28, 2012.

(51) Int. Cl.
*G16H 50/50* (2018.01)
*G06F 17/50* (2006.01)
(Continued)

(52) U.S. Cl.
CPC ............ *G06K 9/6207* (2013.01); *G06T 7/143* (2017.01); *G06T 7/149* (2017.01); *G16H 50/50* (2018.01); *G06F 17/5009* (2013.01); *G06K 9/00496* (2013.01); *G06T 2207/10016* (2013.01); *G06T 2207/10076* (2013.01);
(Continued)

(58) Field of Classification Search
None
See application file for complete search history.

(56) References Cited

U.S. PATENT DOCUMENTS

2011/0112808 A1* 5/2011 Anderson et al. ............... 703/2
2012/0022843 A1* 1/2012 Ionasec et al. .................. 703/9
(Continued)

OTHER PUBLICATIONS

Y. Zheng, A. Barbu, B. Georgescu, M. Scheuering, and D. Comaniciu, "Four-Chamber Heart Modeling and Automatic Segmentation for 3D Cardiac CT Volumes Using Marginal Space Learning and Steerable Features", pp. 1-14, 2008.*
(Continued)

*Primary Examiner* — Kibrom K Gebresilassie

(57) ABSTRACT

A method and system for patient-specific cardiac electrophysiology is disclosed. Particularly, a patient-specific anatomical model of a heart is generated from medical image data of a patient, a level-set representation of the patient-specific anatomical model is generated of the heart on a Cartesian grid; and a transmembrane action potential at each node of the level-set representation of the of the patient-specific anatomical model of the heart is computed on a Cartesian grid.

45 Claims, 3 Drawing Sheets

(51) Int. Cl.
  *G06K 9/62* (2006.01)
  *G06T 7/143* (2017.01)
  *G06T 7/149* (2017.01)
  *G06K 9/00* (2006.01)

(52) U.S. Cl.
  CPC .......... *G06T 2207/10132* (2013.01); *G06T 2207/20161* (2013.01); *G06T 2207/30048* (2013.01)

(56) References Cited

U.S. PATENT DOCUMENTS

| | | | |
|---|---|---|---|
| 2013/0035738 A1* | 2/2013 | Karst et al. ............... | 607/25 |
| 2013/0197881 A1* | 8/2013 | Mansi ................ | A61N 1/3627 703/2 |
| 2014/0088943 A1* | 3/2014 | Trayanova et al. ........... | 703/11 |
| 2015/0042646 A1* | 2/2015 | Comaniciu ............ | G06T 17/20 345/420 |
| 2015/0242588 A1* | 8/2015 | Audigier ............... | A61B 34/10 606/41 |
| 2016/0022369 A1* | 1/2016 | Audigier ................ | G09B 5/02 434/268 |
| 2016/0058520 A1* | 3/2016 | Yang ..................... | G16H 50/50 703/11 |
| 2017/0185740 A1* | 6/2017 | Seegerer ............. | G09B 23/288 |
| 2017/0330075 A1* | 11/2017 | Tuysuzoglu ............ | G06N 3/08 |

OTHER PUBLICATIONS

H. Yoshida, M. Nagaoka, "Multiple relaxation time lattice Boltzmann model for the convection and anisotropic diffusion equation", pp. 7774-7795, 2010.*

C. Mitchell, D. Schaeffer, "A Two Current Model for the Dynamics of Cardiac Membrane" pp. 767-793, 2003.*

Y. Zheng, A. Barbu, B. Georgescu, M. Scheuering, and D. Comaniciu, "Four-Chamber Heart Modeling and Automatic Segmentation for 3D Cardiac CT Volumes Using Marginal Space Learning and Steerable Features" 2008 IEEE.*

C. Mitchell, and D. Schaeffer, "A Two-Current Model for the Dynamics of Cardiac Membrane" 2003.*

H. Yoshida, M. Nagaoka, "Multiple relaxation time lattice Boltzmann model for the convection and anisotropic diffusion equation" 2010.*

Aidun, C.K., et al, "Lattice-Boltzmann Method for Complex Flows", Annual review of Fluid Mechanics, vol. 42 No. 1, pp. 439-472, 2010.

Chen, S., et al, "Lattice Boltzman Method for Fluid Flows", Annual Review of Fluid Mechanics, vol. 30 No. 1, pp. 329-364, 1998.

Clayton R., et al, "Models of Cardiac Tissue Electrophysiology: Progress, Challenges and Open Questions", Progress in Biophysics and Molecular Biology vol. 104 Nos. 1-3, 22, 2011.

Dawson, S.P., et al, "Lattice Boltzmann Computations for Reaction-Diffusion Equations", The Journal of Chemical Physics vol. 98 No. 2, pp. 1514-1523, 1993.

Fillard, P., et al, "Measuring Brain Variability by Extrapolating Sparse Tensor Fields Measured on Sulcal Lines", vol. 3 No. 2, pp. 639-650, Jan. 2007.

Hodgkin, A, et al, "A Quantitative Description of Ion Currents and its Applications to Conduction and Excitation in Nerve Membranes", Journal of Physiology vol. 117 No. 4, pp. 500-544, 1952.

Mitchell, C., et al, "A Two-Current Model for the Dynamics of Cardiac Membrane", Bulletin of Mathematical Biology vol. 65 No. 5, p. 767-793, 2003.

Pop, M., et al, "Fusion of Optical Imaging and MRI for the Evaluation and Adjustment of Macroscopic Models of Cardiac Electrophysiology: A Feasibility Study", Medical Image Analysis vol. 13 No. 2, pp. 370-380, 2009.

Relan, J., et al, "Coupled Personalization of Cardiac Electrophysiology Models for Prediction of Ischaemic Ventricular Tachycardia", Journal of the Royal Society Interface Focus vol. 1 No. 3, pp. 396-407, 2011.

Yoshida, H., et al, "Multiple-Relaxation-Time Lattice Boltzmann Model for the Convection and Anisotropic Diffusion Equation", J. Comput. Phys. vol. 229, pp. 7774-7795, http://dx.doi.org/10.1016/j.jcp.2010.06.037, Oct. 2010.

Yu, D., et al, "Viscous Flow Computations with the Method of Lattice Boltzmann Equation", Progress in Aerospace Sciences vol. 39 No. 5, pp. 329-367, 2003.

Zheng, Y., et al, "Four-Chamber Heart Modeling and Automatic Segmentation for 3-D Cardiac CT Volumes Using Marginal Space Learning and Steerable Features", IEEE Transactions on Medical Imaging vol. 27, No. 11, pp. 1668-1681, 2008.

Dikici, et al., "Quantification of Delayed Enhancement MR Images", In Proc. MICCAI 2004, LNCS 3216, pp. 250-257, 2004.

* cited by examiner

METHOD AND SYSTEM FOR FAST PATIENT-SPECIFIC CARDIAC ELECTROPHYSIOLOGY SIMULATIONS FOR THERAPY PLANNING AND GUIDANCE

This application claims the benefit of U.S. Provisional Application No. 61/604,132, filed Feb. 28, 2012, the disclosure of which is herein incorporated by reference.

BACKGROUND OF THE INVENTION

The present invention relates to the computation of advanced cardiac parameters from medical data and images by using patient-specific multi-physics fluid-solid models of the heart.

The heart is the pump of life. The periodic contraction and relaxation cycle of the heart ensures blood circulation throughout the body. Heart disease, particularly heart rhythm abnormality, can lead to impaired cardiac function and eventually death. Current treatments require careful planning and guidance for optimal outcomes. Computational models of cardiac electrophysiology are being proposed for therapy planning but current approaches are either too simplified or too computationally intensive for patient-specific simulations in day-to-day clinical practice.

Heart rhythm abnormality diagnosis and therapy planning are made difficult by the large variability in heart diseases. Every patient is unique. The variability observed among patients with the same disease is such that population-wise guidelines can be sub-optimal in terms of diagnosis, therapy outcome and complications for a specific patient. For example, patients with acute myocardium infarction can present with variable scar morphology and extent, which can influence the outcome of various cardiac therapies. Accordingly, a framework to assess the current state of the heart and the optimal therapy for a specific patient is desirable. Such a framework should be integrative and comprehensive, considering all major aspects of heart function, and focus on the end-result of any cardiac therapy, which is the propagation of electrical waves across the heart. Computational models of cardiac electrophysiology have been proposed, but are typically either too simplified or too computationally intensive for patient-specific simulations in every day clinical practice.

BRIEF SUMMARY OF THE INVENTION

The present invention provides a method and system for patient-specific cardiac electrophysiology simulation. Embodiments of the present invention can be used to solve cardiac electrophysiology models at or near real-time, for any type of mono-domain cell model. In one embodiment, the method is illustrated on the mono-domain Mitchell-Schaeffer model. The domain is discretized on a Cartesian grid. The cell model is calculated node-wise, while the trans-membrane potential is determined using Lattice-Boltzmann method (LBM-EP). The Lattice-Boltzmann algorithm is inherently parallelizable and is ideally suited for multi-processor environments as well as modern graphical computing units. This results in fast and detailed models of cardiac electrophysiology which can be used for therapy planning. In one embodiment of the present invention, a patient-specific anatomical model of a heart is generated from medical image data of a patient. A level-set representation of the patient-specific anatomical model of the heart is generated on a Cartesian grid and the nodes external to the myocardium are ignored. The transmembrane action potential is simulated at each node of the level-set representation of the patient-specific anatomical model of the heart on a Cartesian grid.

These and other advantages of the invention will be apparent to those of ordinary skill in the art by reference to the following detailed description and the accompanying drawings.

DETAILED DESCRIPTION

The present invention relates to a method and system for patient-specific cardiac electrophysiology simulations based on preoperative medical image data, such as MRI and/or Ultrasound data. Embodiments of the present invention are described herein to give a visual understanding of the cardiac electrophysiology simulation methods. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, it is to be understood that embodiments of the present invention may be performed within a computer system using data stored within the computer system.

Figure 1:
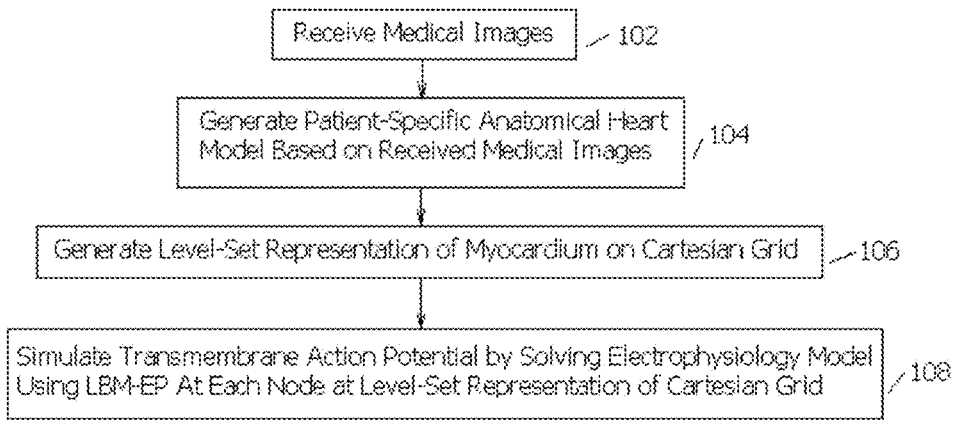
FIG. 1 illustrates a method for patient-specific cardiac electrophysiology simulation according to an embodiment of the present invention.

FIG. 1 illustrates a method for patient-specific cardiac electrophysiology simulation according to an embodiment of the present invention. As illustrated in FIG. 1, at step 102, medical image data is received. The medical image data can be one or more 3D medical images of the patient. The medical images may be a dynamic sequence of medical images, such as a sequence of MR cine images, acquired over at least one complete heart cycle. In advantageous embodiments of the present invention, the medical images can be MRI images and/or ultrasound images, but the present invention is not necessarily limited to these imaging modalities. The medical images may be received directly from a medical imaging device, such as an MR or ultrasound scanner, or the medical images may be received by loading stored medical images of a patient. In addition to medical image data, other patient specific clinical data can also be acquired, including non-imaging patient-specific measurements, such as ECG, body surface mappings, etc.

At step 104, a patient-specific anatomical heart model is generated based on the medical image data of the patient. In one embodiment, the patient-specific anatomical heart model is an anatomical model of the left and right ventricles of the patient's heart.

Figure 2:
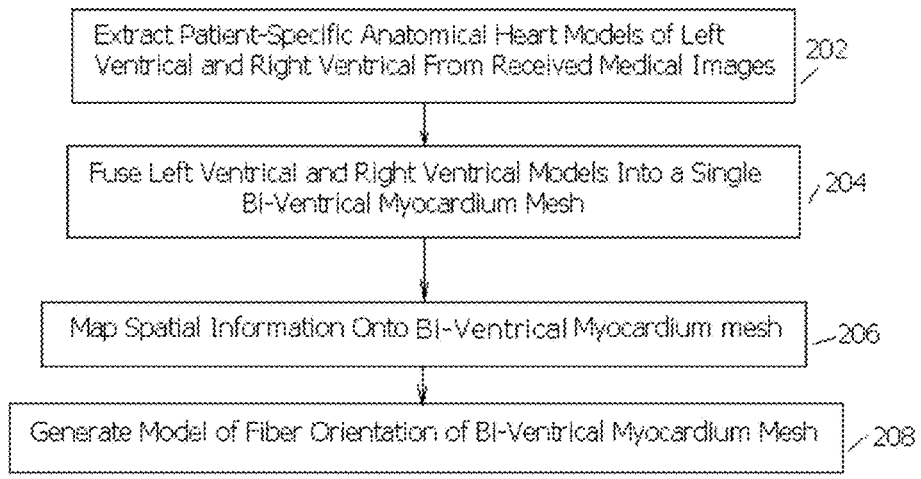
FIG. 2 illustrates a method for generating a patient-specific anatomical model of the left and right ventricles according to an embodiment of the present invention.

FIG. 2 illustrates a method for generating the patient-specific anatomical model of the left and right ventricles according to an embodiment of the present invention. The method of FIG. 2 can be used to implement step 104 of FIG. 1. At step 202, anatomical models of the LV and RV are extracted from the medical images. In an advantageous embodiment, the LV and RV anatomical models show patient-specific heart morphology and dynamics, and are calculated automatically from MRI or ultrasound images. The LV and RV models can be detected in any medical imaging modality (e.g., US or cardiac MR) that covers the entirety of both cardiac ventricles. The LV and RV models can be extracted by segmenting the left endocardium, right endocardium, epicardium, and left and right outflow tract using a marginal space-learning based machine learning method. Obtained triangulations (meshes) are automatically labeled according to the anatomy they represent for subsequent processing.

For each of the LV and the RV, the heart chamber segmentation can be formulated as a two-step learning problem: anatomical structure localization and boundary delineation. In an advantageous embodiment, marginal space learning (MSL) can be used to apply machine learning to 3D object detection. The idea of MSL is not to learn a monolithic classifier directly in the full similarity transformation parameter space but to incrementally learn classifiers on marginal spaces. In particular, the detection of each heart chamber can be split into three problems: position estimation, position-orientation estimation, and position-orientation-scale estimation. A separate classifier is trained based on annotated training data for each of these estimation problems. The classifiers in the lower dimensional marginal spaces are used to prune the searching space efficiently. This object localization stage results in an estimated transformation (position, orientation, and scale) of the object (e.g., heart chamber).

After automatic object localization, the mean shape model of the object is aligned with the estimated transformation to get a rough estimate of the object shape. The shape is then deformed locally to fit the object boundary. Active shape models (ASM) can be used to deform an initial estimate of a non-rigid shape under the guidance of the image evidence and the shape prior. However, a non-learning based generic boundary detector, as used in conventional ASM applications, does not work effectively in heart chamber deformation due to the complex background and weak edges. Instead, a learning based boundary detector can be used to exploit more image evidences to achieve robust boundary detection. Additional details regarding MSL-based heart chamber segmentation are described in U.S. Pat. No. 7,916,919, issued Mar. 29, 2011, and entitled "System and Method for Segmenting Chambers of a Heart in a Three Dimensional Image", United States Published Patent Application No. 2010/0040272, and United States Published Patent Application No. 2012/0022843, which are incorporated herein by reference.

At step 204, the patient-specific LV and RV models are fused into a single bi-ventricular myocardium volumetric mesh. In a possible implementation, the LV and RV anatomies extracted can be fused together. The resulting closed surface is used to create a volumetric, tetrahedral mesh on which vertices are tagged into surface zones according to the underlying anatomy.

At step 206, spatial information is mapped onto the bi-ventricular myocardium mesh. Spatial information, such as scars, grey zones, and fibrosis can be identified in images, such as late delayed-enhancement MR images and mapped onto the bi-ventricular myocardium mesh. For example, scar locations and extent can be segmented in delayed-enhancement MR images using the method described in Dikici et al, "Quantification of Delayed Enhancement MR Images", In Proc. MICCAI 2004, LNCS 3216, pp 250-257, 2004, which is incorporated herein by reference. The scar information is mapped onto the bi-ventricular myocardium mesh by tagging the tetrahedral elements that lie within the segmented scar regions. This spatial information is important to simulate the electrical wave around scars, in particular for wave-reentry assessment, but also the impaired contractility due to dead tissue.

At step 208, a model of fiber orientation is generated on the bi-ventricular myocardium mesh. In one embodiment, in-vivo diffusion tensor (DT) MR images of the patient's cardiac fibers can be directly mapped to the anatomical model through image registration. In this case, the DT MR image is non-linearly registered to the medical image in which the LV and RV models are detected. The resulting transformation is used to deform the tensor field in the DT MR image towards the anatomical model. The Finite Strain method, the details of which are described in Peyrat et al., "A Computational Framework for the Statistical Analysis of Cardiac Diffusion Tensors: Application to a Small Database of Canine Hearts", IEEE TMI, 26(11):1500-1514, 2007, which is incorporated herein by reference, is used to reorient the tensors once the tensors are registered to the anatomical model.

In another embodiment, if no in-vivo DT MRI is available, the model of fiber orientation may be computed directly from the anatomical model using a rule-based method. A generic model of myocardium fiber architecture that includes fiber and fiber sheets is computed. A rule-based strategy is followed to generate the fiber architecture to cover the entire bi-ventricular myocardium from apex to valves. Below the basal plane, which is identified automatically using point correspondences of the initial triangulations of the anatomical model, the fiber elevation angle with respect to the short axis plane varies linearly across the myocardium, from −70° on the epicardium to +70° on the endocardium. The fiber and sheet orientations are then fixed around each valve. In particular, fibers are longitudinal around the aortic valve and tangential around the mitral, tricuspid, and pulmonary valves, and sheet normals are oriented towards the barycenter of the valves. The local orthonormal basis is then interpolated from the basal plane to the valve, first by following the myocardium surface, then throughout the myocardium thickness. For orthonormality preservation, the interpolation can be performed using a Log-Euclidean framework. Additional details regarding generating the patient-specific anatomical model are described in U.S. patent application Ser. No. 13/754,174, entitled "Method and System for Patient Specific Planning of Cardiac Therapies on Preoperative Clinical Data and Medical Images", filed Jan. 30, 2013, which is incorporated herein by reference.

Returning to FIG. 1, at step 106, a level-set representation of myocardium from the bi-ventricular mesh (anatomical model) is generated on a Cartesian grid. It is to be understood that a level-set representation of the domain boundaries may be used to ensure proper boundary conditions for image-based patient-specific anatomies. The nodes of the Cartesian grid which lie outside the myocardium are not relevant for electrophysiology and are eliminated for computational performance. At step 108, the patient's cardiac electrophysiology is computed by calculating diffusion of transmembrane potential across the level-set representation of the myocardium using the Lattice-Boltzmann method (LBM-EP) to solve for a cardiac electrophysiology model.

The Lattice-Boltzmann Method is applicable to a large class of electrophysiology models, known as the mono-domain models. In one embodiment, the mono-domain Mitchell-Schaeffer model of cardiac action potential can be used as an electrophysiology model to characterize action potential across the patient's myocardium. The Mitchell-Schaeffer model is described in Mitchell et al., "A Two-Current Model for the Dynamics of Cardiac Membrane", *Bulletin of Mathematical Biology*, 65(5):767-793, 2003, which is incorporated herein by reference. It is to be understood that other known mono-domain cellular models, such as TenTusscher model, Fenton and Karma model, and Noble model, can be applied to the system and method described in the present application.

The Mitchell-Schaeffer model relates the normalized transmembrane action potential $\upsilon(t) \in [0,1]$ to an inward gated current $J_{in} = h\upsilon^2(1\upsilon)/\overline{\tau in}$, which captures the fast acting currents, and an outward un-gated current $J_{out} = -\upsilon/\tau_{out}$, which accounts for transmembrane voltage decrease. A transient stimulus current $J_{stim}$ is added to the model to simulate electrical pacing. The following equations are solved to compute the generation and propagation of the action potential over patient's bi-ventricular geometry:

$$\frac{\partial \upsilon}{\partial t} = J_{int} + J_{out} + J_{stim} + c\nabla \cdot D\nabla \upsilon, \quad (1)$$

$$\frac{dh}{dt} = \begin{cases} \frac{1-h}{\tau_{open}} & \text{if } \upsilon < \upsilon_{gate} \\ \frac{-h}{\tau_{close}} & \text{if } \upsilon \geq \upsilon_{gate}, \end{cases} \quad (2)$$

where, h(t) is a gating variable that models the state of the ion channels, $D = \rho Id + (1-\rho)aa^T$ is the anisotropic diffusion tensor along the fiber direction $\alpha$ with anisotropy ratio $\rho$, c the diffusion coefficient along the fibers, and $\upsilon_{gate}$ is the change-over voltage. The diffusion tensor varies considerably between the different structures in the heart, with fast conduction along Purkinje fibers and very slow conduction through the scarred regions. The Lattice-Boltzmann method can accurately address there spatial inhomogeneities. $\rho_{in}$, $\tau_{out}$, $\tau_{open}$, and $\tau_{close}$ are free parameters that directly related to the shape and duration of the action potential, which makes possible their calibration from clinical data.

In an advantageous embodiment, to solve equations (1) and (2) the domain is discretized using a 3D Cartesian lattice with 7 connectivities (6 connections to the nearest nodes on the lattice+central position). Equation (2) is solved at every node using an explicit time scheme while Equation (1) is solved using Lattice-Boltzmann method (LBM). In one embodiment, the Rush and Larsen method, which is described in S. Rush and H. Larsen, "A practical algorithm for solving dynamic membrane equations", IEEE Transactions on Biomedical Engineering, Vol. BME-25, Issue 4, Pages 389-392, 1978, which is incorporated herein by reference, is used to solve Equation (2). The fundamental variable of LBM is the vector of distribution functions $f(x) = \{f_i(x)\}_{i=1 \ldots 7}$, where $f_i(x)$ represents the probability of finding a particle traveling along the $i^{th}$ edge $e_i$ of node x. The governing equation for the $i^{th}$ edge at x is composed of two mathematical steps:

$$f_i = f_i - A_{ij}(f_j - \omega_j \upsilon) + \delta t \omega_i R(\upsilon, \{h\}), \quad (3)$$

$$f_i(x + e_i \delta t, t + \delta t) = f_i(x, t) \quad (4)$$

where, the collision matrix $A = (A_{ij})_{i,j} \in [[1,7]]$ relaxes the distribution function $f_i$ towards the local value of the potential, $\upsilon$, $R(\upsilon, \{h\})$ is the set of currents from the cellular model, which depends on the set of model-dependent internal variables $\{h\}$ and $\omega_i$ is a weighting factor that depends on lattice connectivity. In one embodiment, $\omega_i = 1/8$ for the edges to the six neighbors and $\omega_i = 1/4$ for the central position. For the Mitchell and Schaeffer model, $R(\upsilon, \{h\}) = J_{in} + J_{out} + J_{stim}$.

The transmembrane action potential is related to the distribution functions $f_i$ through $\upsilon(x,t) = \Sigma_i f_i(x, t)$. In each computational time step $\delta t$, a strictly local collision rule is applied to the distribution functions at each node (Equation (3)). For post-collision, the distribution functions move along their corresponding edges to the neighboring nodes (Equation (4)).

In an embodiment, the collision matrix A is assumed to relax each component towards the local potential by a characteristic relaxation time $\tau$, $A = (1/\tau)I$ where I is the 7×7 identity matrix. At the problem boundaries, the streaming step requires the specification of incoming distribution functions. It can be shown that diffusion flux at a node is related to the distribution function through $c\nabla \upsilon = (1 - 1/2\tau)\Sigma_i f_i e_i$. For a boundary with local normal n, requiring $\nabla \upsilon \cdot n = 0$ implies $\Sigma_i f_i e_i \cdot n = 0$. If the boundary is normal to any edge of the lattice, the Neumann boundary condition is automatically recovered if the incoming distribution at the node is equal to the outgoing distribution. For complex geometries, a better description of the manner in which the edges of the lattice are intersected by the curved geometry may be required. To this extent, a level set formulation is used to obtain the distance to the wall at nodes close to the boundary. Interpolation based on this distance is used to implement the boundary conditions. Interpolation to implement the boundary conditions based on a distance is described in detail by Yu et al., "Viscous Flow Computations with the Method of Lattice-Boltzmann Equation", *Progress in Aerospace Sciences*, 39(5), 329-367 (2003), which is incorporated herein by reference.

Equations (3)-(4) can be utilized along with $A = (1/\tau)I$ to reproduce the reaction-diffusion equation (Equation (1)) with an isotropic diffusion coefficient of $c = (2\tau 1)/-8$. This method can also be utilized to model the complete anisotropic diffusion tensor. In this case, instead of the single relaxation time approximation, the matrix A is defined as $A = M^{-1}SM$,
where in one embodiment $$M = \begin{pmatrix} 1 & 1 & 1 & 1 & 1 & 1 & 1 \\ 0 & -1 & 0 & 0 & 0 & 0 & 0 \\ 0 & 0 & 1 & -1 & 0 & 0 & 0 \\ 0 & 0 & 0 & 0 & 1 & -1 & 0 \\ 1 & 1 & 1 & 1 & 1 & 1 & -6 \\ 1 & 1 & -1 & -1 & 0 & 0 & 0 \\ 1 & 1 & 1 & 1 & -2 & -2 & 0 \end{pmatrix}$$

$$S^{-1} = \begin{pmatrix} \tau_1 & 0 & 0 & 0 & 0 & 0 & 0 \\ 0 & \tau_{22} & \tau_{23} & \tau_{24} & 0 & 0 & 0 \\ 0 & \tau_{32} & \tau_{33} & \tau_{34} & 0 & 0 & 0 \\ 0 & \tau_{42} & \tau_{43} & \tau_{44} & 0 & 0 & 0 \\ 0 & 0 & 0 & 0 & \tau_5 & 0 & 0 \\ 0 & 0 & 0 & 0 & 0 & \tau_6 & 0 \\ 0 & 0 & 0 & 0 & 0 & 0 & \tau_7 \end{pmatrix}.$$

M is a matrix that transforms the vector of distribution functions to a set of moments and the method is not limited to the choice presented above. The first row of M corresponds to $\upsilon = \Sigma_i f_i$, while rows 2 through 4 are the three components of the diffusion flux. The rest of the moments are higher-order quantities which do not affect the diffusion problem and can be optimized for greater stability. The relaxation times $(\tau_{ij})_{i,j} \in [[1,3]]$ are related to the components of the diffusion tensor through $$T_{ij} = \frac{\delta_{ij}}{2} + \frac{D_{ij}\delta t}{[(c)_s^2 \delta x^2]},$$

where $c_s^2$ is a parameter which depends on the choice of $\omega_i$ and equals ¼ for the choice presented above. The relaxation times $\tau_5$, $\tau_6$, and $\tau_7$ related to the higher order moments do not directly effect the diffusion solution, but effect the stability of the method. In an embodiment of the present invention, $\tau_1=1$, and $\tau_5=\tau_6$ $\tau_7=1.33$. It is to be understood that, although the present application illustrates a system and method using 7 connectivities, the electrophysiology model described in the present application can be implemented with higher number of connectivities, such as 15-, 19-, 27-connectivities, and higher, for increased accuracy and stability.

Figure 3:
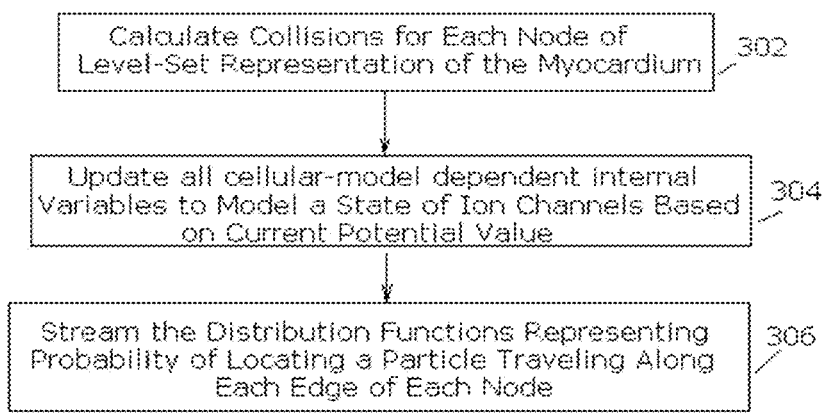
FIG. 3 illustrates a method of simulating cardiac electrophysiology using a Lattice-Boltzmann method according to an embodiment of the present invention.

FIG. 3 illustrates a method of simulating cardiac electrophysiology using a Lattice-Boltzmann method (LBM-EP), according to an embodiment of the present invention. It is to be understood that the method of FIG. 3 can be used to implement step 108 of FIG. 1. Referring to FIG. 3, at step 302, at a current time step, collisions $f_i(x)$ for each node of the level set representation of the myocardium are calculated. That is the distribution function $f_i(x)$ for edge (e.g., i=1 . . . 7) is calculated for each node using Equation 3. The collisions calculated for each node are used to calculated the action potential at each node as $\upsilon(x,t)=\Sigma_i f_i(x,t)$. At step 304, the cellular-model dependent internal variables are updated. In case of the Mitchell and Schaeffer model, the gating variable h(t) is updated for the current time step using Equation (2) to model a state of ion channels based on current potential value. At step 306, the distribution functions representing probability of locating a particle traveling along each edge of each node are streamed. That is, post-collision, the distribution functions move along their corresponding edges to the neighboring nodes and Equation (4) is used to calculate the distribution functions at the next time step as a result of this streaming. Steps 302, 304, and 306 of FIG. 3 can then be repeated for a number of iterations representing a number of time steps. At each iteration, the current time is advanced by a predetermined step size.

In an exemplary implementation. the method of FIG. 3 can be implemented in any type of programming language using the following algorithm:

```
1: for iter = 1 → nbIter do
2:   t ← t + δt
3:   for every node x do
4:     for i = 1 → 7 do
5:       Compute collisions f_i(x)
6:       Compute transmembrane action potential υ(x,t) = Σ_i f_i(x,t)
7:     Update h(x)
8:   for every node x do
9:     for i = 1 → 7 do
10:      Stream f_i(x)
11: return υ, h
```

One skilled in the art will appreciate that, while in one embodiment of the present invention, the nodes are processed sequentially, the approach described above can be extended to parallel architecture.

In order to personalize the electrophysiology model to a specific patient, the parameters of the electrophysiology model can be adjusted using inverse problem methods based on the observed clinical data and medical image data for the patient. For example, ECG and endocardial mapping are used to adjust tissue diffusivity and action potential duration, mainly controlled by the parameter $\tau_{close}$, at every node of the anatomical model. For example, the simulated QRS (heartbeat) can be aligned with measured QRS by adjusting tissue diffusivity. If endocardial mappings are available, inverse problem methods can be used to estimate tissue conductivity and by comparing the simulated isochrones and potentials with measurements. Additionally, dynamic images can be used to adjust electrophysiology overall synchrony by minimizing the difference of the visible cardiac motion and calculated activation times, and bundle branch blocks can be simulated by modifying the activation times of the left and right ventricles as well as the diffusivity of the respective macro-scale model of Purkinje network/His bundle.

Returning to FIG. 1, at step 108, the patient-specific electrophysiology computation results are output. In particular, the values of the transmembrane potential for each node of the anatomical model can be output over time. The output electrophysiology computation results can be used as input into a full computational heart model, for example, to compute movements of the heart tissue in response to the action potential, and to compute blood-flow using fluid-structure interaction (FSI) simulations based on the movement of the heart tissue.

In order to illustrate the effectiveness of the system and method described in the present application over the existing systems and methods, the system and method described in the present application (denoted as LBM-EP) was practically compared with a first-order, semi-implicit finite element (FEM) implementation of Mitchell-Schaeffer model, denoted (FEM-EP). All the experiments were executed on a standard desktop machine (Intel Xeon, 2.40 GHz octo-core, 4 GB RAM) with 32b Windows XP. FEM-EP relied on linear tetrahedra with first order quadrature. The stiffness matrix was built using parallel optimization (OpenMP) to increase computational efficiency. It is to be understood that, to achieve higher efficiency, the system and method described in the present application can be implemented using Graphics Processing Unit (GPU) or multi-processor architectures for near real-time electrophysiology simulation.

LBM-EP and FEM-EP Comparison. A 10×10×0:5 cm slab was discretized in 401×401×3 nodes (1,920,000 tetrahedra for FEM-EP). For both LBM-EP and FEM-EP, the variables were set as following: $\tau_{close}$=150 ms, $\tau_{open}$=120 ms, $\tau_{in}$=0:3 ms, $\tau_{out}$=6 ms, $\upsilon_{gate}$=0:13, c=0.0003 cm$^2$/s and ρ=1 (isotropic diffusion). An electrical stimulation was applied at the nodes (x=0; y; z) during $t_{stim}$=1 ms by setting υ=1 at these nodes. The time step was δt=0:5 ms for both models. Three different experiments were carried out to test the models in different conditions: front propagation, front propagation with scar, and vortex formation.

Figure 4:
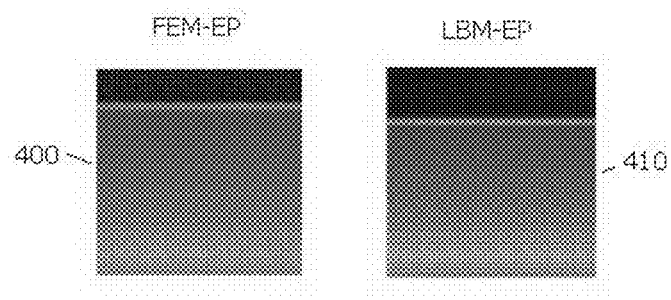
FIG. 4 illustrates exemplary simulation results of front propagation simulation.

FIG. 4 illustrates exemplary simulation results of front propagation in a homogeneous medium. As shown in FIG. 4 images 400 and 410 show a snapshot of the front propagation simulation in a homogeneous medium using FEM-EP and LBM-EP, respectively. In images 400 and 410, the shading represents the transmembrane potential. As illustrated on FIG. 4, both models (FEM-EP 400 and LBM-EP 410) generated similar results.

Figure 5:
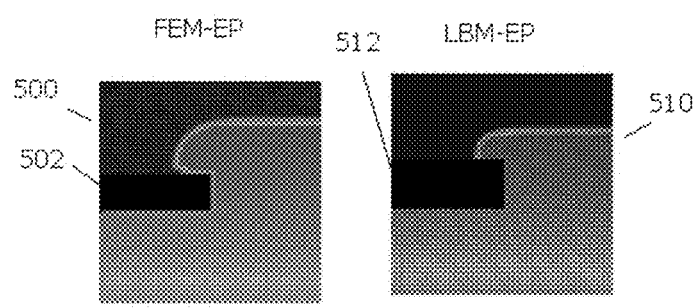
FIG. 5 illustrates exemplary simulation results of front propagation with scar tissue.

FIG. 5 illustrates exemplary simulation results of front propagation with scar tissue. As shown in FIG. 5, images 500 and 510 show a snapshot of the front propagation with scar tissue simulation using FEM-EP and LBM-EP, respectively. The behavior of LBM-EP was verified in the presence of a scar by setting the diffusion coefficient c=0 to nodes in the middle of the domain of the scar tissue. In this simulation, LBM-EP correctly captured the bending of the front around the scar 512, an important feature when simulating pathology. Accordingly, the LBM-EP model 510 performs similarly to the FEM-EP 500, which also captures the bending of the front around the scar 502.

Figure 6:
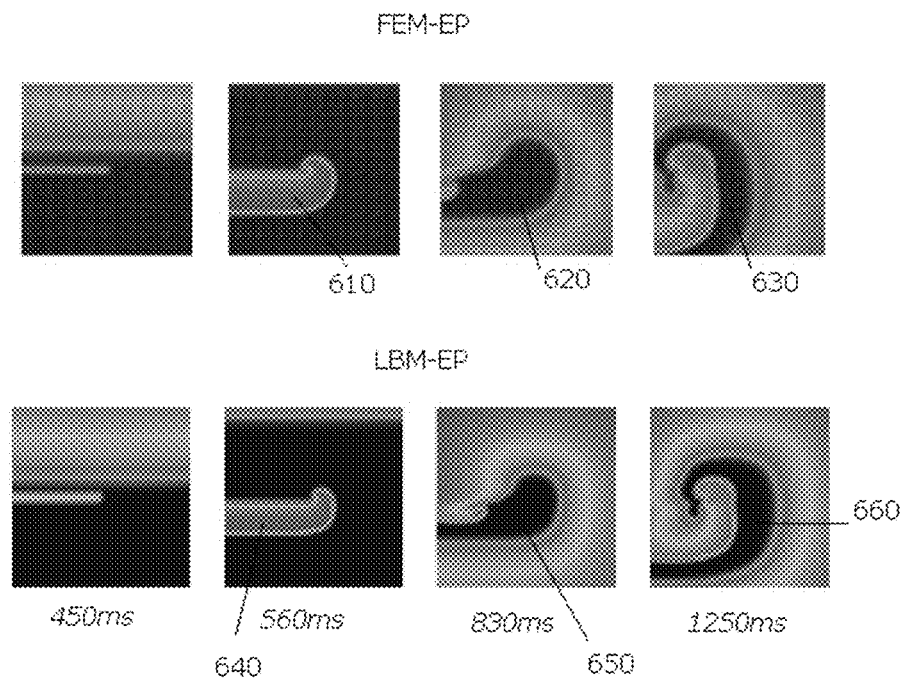
FIG. 6 illustrates exemplary simulation results showing vortex initiation due to premature stimulation.

FIG. 6 illustrates exemplary simulation results showing vortex initiation due to premature stimulation. Specifically, FIG. 6 illustrates the ability of LBM-EP to simulate vortex formation due to premature stimulation. In this case, the scar was removed but a second stimulation was applied in the middle of the domain at t=452 ms. FIG. 6 illustrates the isochrones at different simulation times (e.g., 450 ms, 560 ms, 830 ms, and 1250 ms) using FEM-EP and LBM-EP. A vortex appeared in both models, with qualitatively similar patterns. For example vortex 610 detected by FEM-EP at time stamp 560 ms is similar to the vortex 640 detected by LBM-EP at the same time stamp (i.e., 560 ms). Similarly, vortices 620 and 630 detected by FEM-EP respectively at 830 ms and at 1250 ms are similar to the vortexes 650 and 660 detected by LBM-EP respectively at 830 ms and at 1250 ms.

The above described experiments illustrate that LBM-EP is capable of capturing the main electrophysiology phenomenon. Furthermore and most importantly, the LBM method results in a significant increase in speed over the use of the finite element model and was approximately 10 times faster without particular optimization or parallelization.

Figure 7:
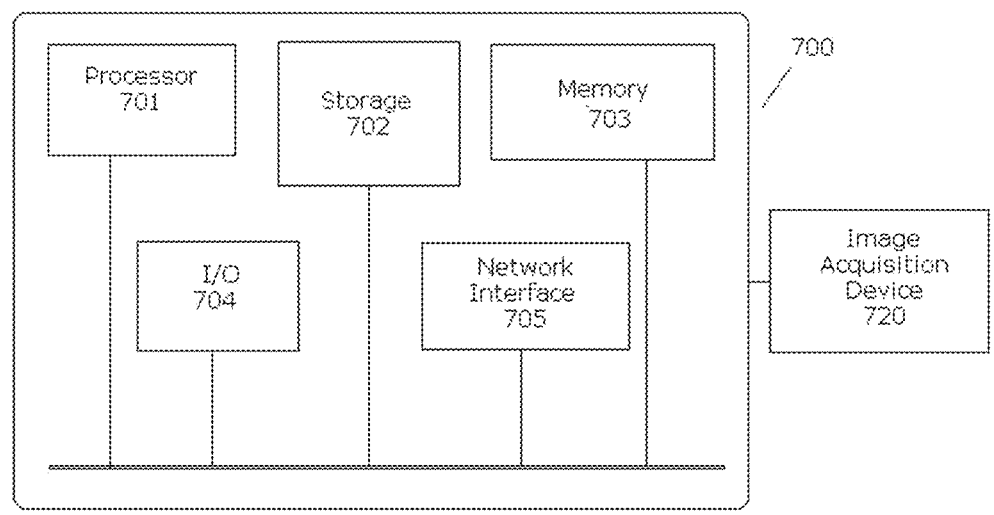
FIG. 7 is a high-level block diagram of a computer capable of implementing the present invention.

The above-described methods for generating a patient-specific anatomic model of the heart, generating a patient-specific computational model of the heart, and performing patient-specific cardiac therapy simulations can be implemented on a computer using well-known computer processors, memory units, storage devices, computer software, and other components. A high-level block diagram of such a computer is illustrated in FIG. 7. Computer 702 contains a processor 704, which controls the overall operation of the computer 702 by executing computer program instructions which define such operation. The computer program instructions may be stored in a storage device 712 (e.g., magnetic disk) and loaded into memory 710 when execution of the computer program instructions is desired. Thus, the steps of the methods of FIGS. 1-4 may be defined by the computer program instructions stored in the memory 710 and/or storage 712 and controlled by the processor 704 executing the computer program instructions. An image acquisition device 720, such as an MR scanning device, Ultrasound device, etc., can be connected to the computer 702 to input image data to the computer 702. It is possible to implement the image acquisition device 720 and the computer 702 as one device. It is also possible that the image acquisition device 720 and the computer 702 communicate wirelessly through a network. The computer 7902 also includes one or more network interfaces 706 for communicating with other devices via a network. The computer 702 also includes other input/output devices 708 that enable user interaction with the computer 702 (e.g., display, keyboard, mouse, speakers, buttons, etc.). Such input/output devices 708 may be used in conjunction with a set of computer programs as an annotation tool to annotate volumes received from the image acquisition device 720. One skilled in the art will recognize that an implementation of an actual computer could contain other components as well, and that FIG. 7 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for patient-specific cardiac electrophysiology computations, comprising:
   generating a patient-specific anatomical model of a heart from medical image data of a patient;
   identifying at least one key electrophysiological structures of interest from the patient-specific anatomical model and medical image data;
   generating a level-set representation of the patient-specific anatomical model of the heart on a Cartesian grid; and
   computing a transmembrane action potential on at least one node of the level-set representation of the patient-specific anatomical model of the heart, wherein computing the transmembrane action potential is based at least in part on a stimulus current input as an initial condition.

2. The method of claim 1, wherein the step of generating a patient-specific anatomical model of a heart from medical image data of a patient comprises:
   detecting a patient-specific left ventricle endocardium model, a patient-specific right ventricle endocardium model, and a patient-specific epicardium model in the medical image data; and
   fusing the left ventricle endocardium model, the right ventricle endocardium model and the epicardium model into a single bi-ventricular volumetric mesh.

3. The method of claim 2, wherein the step of generating a patient-specific anatomical model of a heart from medical image data of a patient further comprises:
   mapping spatial information corresponding to at least one of scars, grey zones, or fibrosis identified from medical-image data and other clinical measurements onto the bi-ventricular volumetric mesh.

4. The method of claim 2, wherein the step of generating a patient-specific anatomical model of a heart from medical image data of a patient further comprises:
   registering a tensor field of an in-vivo diffusion tensor magnetic resonance image of cardiac fibers to the bi-ventricular volumetric mesh.

5. The method of claim 2, wherein the step of generating a patient-specific anatomical model of a heart from medical image data of a patient further comprises:
   generating a global model of fiber architecture based on the bi-ventricular volumetric mesh and nominal values for fiber elevation angle distribution.

6. The method of claim 1, wherein the step of computing the transmembrane action potential on at least one node of the level-set representation of the patient-specific anatomical model of the heart further comprising:
   solving at least one monodomain electrophysiology model using a Lattice-Boltzmann method on at least one node of the level-set representation on a Cartesian grid.

7. The method of claim 1, wherein the step of generating a level-set representation of the patient-specific anatomical model of the heart on a Cartesian grid comprises:
   discretizing a domain of the patient-specific model of the heart using a Cartesian lattice in which each node is connected via edges to a predetermined number of neighboring nodes.

8. The method of claim 1, wherein the step of computing the transmembrane action potential on at least one node of the level-set representation of the patient-specific anatomical model of the heart further comprises:
   at each of a plurality of time steps:
      for at least one node of the level-set representation of the patient-specific anatomical model of the heart on a Cartesian grid,
      calculating collisions of particles for each edge connected to the node based on a distribution function calculated for each edge;
      calculating the transmembrane action potential at the node based on the collisions of particles calculated at the node;
      updating all cellular model-dependent internal variables at the node;
      updating the distribution function for each edge of the node to represent streaming of a particle traveling along each of the edges to a neighboring node; and
      applying optional Dirichlet boundary conditions.

9. The method of claim 8, wherein the step of calculating collisions of particles for each edge connected to the node based on a distribution function calculated for each edge comprises:
   calculating collisions on each edge connected to the node as:
   $$f_i = f_i - A_{ij}(f_j - \omega_j \upsilon) + \delta t \omega_i R(\upsilon, \{h\})$$
   where $f_i$ is the distribution function that represents a probability of finding a particle traveling along the $i^{th}$ edge $e_i$ connected to the node, $A = (A_{ij})_{i,j} \in$ is a collision matrix that relaxes the distribution function $f_i$ towards a local potential value, $\upsilon$, $R(\upsilon, \{h\})$ is a model-dependent term for electrophysiological currents, which depends on a model-dependent set of internal variables $\{h\}$, and $\omega_i$ and $\omega_j$ are weighting factors for edges $e_i$ and $e_j$, respectively.

10. The method of claim 9, wherein the collision matrix A is defined as $A = M^{-1}SM$,
where M is a matrix designed to transform the distribution functions into a vector of moments and $S^{-1}$ is a matrix of relaxation times corresponding to the moments, and M and $S^{-1}$ are respectively defined as:

$$M = \begin{pmatrix} 1 & 1 & 1 & 1 & 1 & 1 & 1 \\ 0 & -1 & 0 & 0 & 0 & 0 & 0 \\ 0 & 0 & 1 & -1 & 0 & 0 & 0 \\ 0 & 0 & 0 & 0 & 1 & -1 & 0 \\ 1 & 1 & 1 & 1 & 1 & 1 & -6 \\ 1 & 1 & -1 & -1 & 0 & 0 & 0 \\ 1 & 1 & 1 & 1 & -2 & -2 & 0 \end{pmatrix}$$

$$S^{-1} = \begin{pmatrix} \tau_1 & 0 & 0 & 0 & 0 & 0 & 0 \\ 0 & \tau_{22} & \tau_{23} & \tau_{24} & 0 & 0 & 0 \\ 0 & \tau_{32} & \tau_{33} & \tau_{34} & 0 & 0 & 0 \\ 0 & \tau_{42} & \tau_{43} & \tau_{44} & 0 & 0 & 0 \\ 0 & 0 & 0 & 0 & \tau_5 & 0 & 0 \\ 0 & 0 & 0 & 0 & 0 & \tau_6 & 0 \\ 0 & 0 & 0 & 0 & 0 & 0 & \tau_7 \end{pmatrix}.$$

11. The method of claim 8, wherein the step of calculating the transmembrane action potential at the node based on the collisions of particles calculated at the node comprises:
   calculating the transmembrane action potential v(x, t) for a node x at time step t as:
   $$\upsilon(x, t) = \Sigma_i f_i(x, t)$$
   where $f_i(x, t)$ represents a probability of finding a particle traveling along the $i^{th}$ edge $e_i$ connected to node x at time step t.

12. The method of claim 8, wherein the step of updating all cellular model-dependent internal variables at the node comprises:
   using an integration scheme to solve a system of model-specific differential-algebraic equations modeling each internal variables.

13. The method of claim 8, wherein the step of updating the distribution function for each edge of the node to represent streaming of a particle traveling along each of the edges to a neighboring node comprises:
   calculating the distribution functions at the next time step as:
   $$f_i(x + e_i \delta t, t + \delta t) = f_i(x, t).$$
   where $f_i(x, t)$ represents a probability of finding a particle traveling along the $i^{th}$ edge $e_i$ connected to node x at time step t.

14. The method of claim 1, wherein the step of identifying key electrophysiology structures of interest from the patient-specific anatomical model and medical image data comprises:
   identifying and tagging surface zones representing electrophysiology structures of the heart using machine learning algorithms; and
   assigning spatially variable electrophysiological properties of myocardial tissue.

15. The method of claim 14, wherein the step of assigning spatially variable properties of the myocardial tissue comprises:
   assigning tissue electrical conductivity and other model-dependent internal parameters estimated from medical image data and other clinical measurements.

16. An apparatus for patient-specific electrocardiography simulation, comprising:

a processor; and a memory storing computer program instructions, which when executed by the processor cause the processor to perform operations comprising:

generating a patient-specific anatomical model of a heart from medical image data of a patient;

identifying at least one key electrophysiological structures of interest from the patient-specific anatomical model and medical image data;

generating a level-set representation of the patient-specific anatomical model of the heart on a Cartesian grid; and computing a transmembrane action potential on at least one node of the level-set representation of the patient-specific anatomical model of the heart, wherein computing the transmembrane action potential is based at least in part on a stimulus current input as an initial condition.

17. The apparatus of claim 16, wherein generating a patient-specific anatomical model of a heart from medical image data of a patient comprises:

detecting a patient-specific left ventricle endocardium model, a patient-specific right ventricle endocardium model, and a patient-specific epicardium model in the medical image data; and fusing the left ventricle endocardium model, the right ventricle endocardium model and the epicardium model into a single bi-ventricular volumetric mesh.

18. The apparatus of claim 17, wherein generating a patient-specific anatomical model of a heart from medical image data of a patient further comprises:

mapping spatial information corresponding to at least one of scars, grey zones, or fibrosis identified from an MR sequences onto a tetrahedral representation of bi-ventricular volumetric mesh.

19. The apparatus of claim 17, wherein generating a patient-specific anatomical model of a heart from medical image data of a patient further comprises:

registering a tensor field of an in-vivo diffusion tensor magnetic resonance image of cardiac fibers to the bi-ventricular volumetric mesh.

20. The apparatus of claim 17, wherein generating a patient-specific anatomical model of a heart from medical image data of a patient further comprises:

generating a global model of fiber architecture based on the bi-ventricular volumetric mesh and nominal values for fiber elevation angle distribution.

21. The apparatus of claim 16, wherein computing the transmembrane action potential on at least one node of the level-set representation of the patient-specific anatomical model of the heart further comprises:

solving at least one monodomain electrophysiology model using a Lattice-Boltzmann method on at least one node of the level-set representation on a Cartesian grid.

22. The apparatus of claim 16, wherein generating a level-set representation of the patient-specific anatomical model of the heart on an isotropic Cartesian grid comprises:

discretizing a domain of the patient-specific model of the heart using a Cartesian lattice in which each node is connected via edges to a predetermined number of neighboring nodes.

23. The apparatus of claim 16, wherein computing the transmembrane action potential on at least one node of the level-set representation of the patient-specific anatomical model of the heart further comprises:

at each of a plurality of time steps:

for at least one node of the level-set representation of the patient-specific anatomical model of the heart on a Cartesian grid, calculating collisions of particles for each edge connected to the node based on a distribution function calculated for each edge;

calculating the transmembrane action potential at the node based on the collisions of particles calculated at the node;

updating all cellular model-dependent internal variables at the node;

updating the distribution function for each edge of the node to represent streaming of a particle traveling along each of the edges to a neighboring node; and applying optional Dirichlet boundary conditions.

24. The apparatus of claim 23, wherein calculating collisions of particles for each edge connected to the node based on a distribution function calculated for each edge comprises:

calculating collisions on each edge connected to the node as:

$f_i = f_i - A_{ij}(f_j - \omega_j \upsilon) + \delta t \omega_i R(\upsilon, \{h\})$ where $f_i$ is the distribution function that represents a probability of finding a particle traveling along the $i^{th}$ edge $e_i$ connected to the node, $A=(A_{ij})_{i,j} \in$ is a collision matrix that relaxes the distribution function $f_i$ towards a local potential value, $\upsilon$, $R(\upsilon, \{h\})$ is a model-dependent term for electrophysiological currents, which depends on a model-dependent set of internal variables $\{h\}$, and $\omega_i$ and $\omega_j$ are weighting factors for edges $e_i$ and $e_j$, respectively.

25. The apparatus of claim 24, wherein the collision matrix A is defined as $A=M^{-1}SM$, where M is a matrix designed to transform the distribution functions into a vector of moments and $S^{-1}$ is a matrix of relaxation times corresponding to the moments, and M and $S^{-1}$ are respectively defined as:

$$M = \begin{pmatrix} 1 & 1 & 1 & 1 & 1 & 1 & 1 \\ 0 & -1 & 0 & 0 & 0 & 0 & 0 \\ 0 & 0 & 1 & -1 & 0 & 0 & 0 \\ 0 & 0 & 0 & 0 & 1 & -1 & 0 \\ 1 & 1 & 1 & 1 & 1 & 1 & -6 \\ 1 & 1 & -1 & -1 & 0 & 0 & 0 \\ 1 & 1 & 1 & 1 & -2 & -2 & 0 \end{pmatrix}$$

$$S^{-1} = \begin{pmatrix} \tau_1 & 0 & 0 & 0 & 0 & 0 & 0 \\ 0 & \tau_{22} & \tau_{23} & \tau_{24} & 0 & 0 & 0 \\ 0 & \tau_{32} & \tau_{33} & \tau_{34} & 0 & 0 & 0 \\ 0 & \tau_{42} & \tau_{43} & \tau_{44} & 0 & 0 & 0 \\ 0 & 0 & 0 & 0 & \tau_5 & 0 & 0 \\ 0 & 0 & 0 & 0 & 0 & \tau_6 & 0 \\ 0 & 0 & 0 & 0 & 0 & 0 & \tau_7 \end{pmatrix}.$$

26. The apparatus of claim 23, wherein calculating the transmembrane action potential at the node based on the collisions of particles calculated at the node comprises:

means for calculating the transmembrane action potential for a node x as:

$\upsilon(x,t) = \Sigma_i f_i(x,t)$ where $f_i(x, t)$ represents a probability of finding a particle traveling along the $i^{th}$ edge $e_i$ connected to node x at time step t.

27. The apparatus of claim 23, wherein updating all cellular model-dependent internal variables at the node comprises:
  using an integration scheme to solve a system of model-specific differential-algebraic equations modeling each of the internal variables.

28. The apparatus of claim 23, wherein updating the distribution function for each edge of the node to represent streaming of a particle traveling along each of the edges to a neighboring node comprises:
  calculating the distribution functions at the next time step as:
  $f_i(x+e_i\delta t, t+\delta t) = f_i(x,t)$
  where $f_i(x,t)$ represents a probability of finding a particle traveling along the $i^{th}$ edge $e_i$ connected to node x at time step t.

29. The apparatus of claim 17, wherein identifying key electrophysiology structures of interest from the patient-specific anatomical model and medical image data comprises:
  identifying and tagging surface zones representing electrophysiology structures of the heart using machine learning algorithms; and
  assigning spatially variable electrophysiological properties of the myocardial tissue.

30. The apparatus of claim 29, wherein assigning spatially variable properties of the myocardial tissue comprises:
  assigning tissue electrical conductivity and other model-dependent internal parameters estimated from medical image data and other clinical measurements.

31. A non-transitory computer readable medium storing computer program instructions for patient-specific electrocardiography simulation, the computer program instructions, when executed, cause a processor to perform a method comprising:
  generating a patient-specific anatomical model of a heart from medical image data of a patient;
  identifying at least one key electrophysiological structures of interest from the patient-specific anatomical model and medical image data;
  generating a level-set representation of the patient-specific anatomical model of the heart on a Cartesian grid; and
  computing a transmembrane action potential on at least one node of the level-set representation of the patient-specific anatomical model of the heart, wherein computing the transmembrane action potential is based at least in part on a stimulus current input as an initial condition.

32. The non-transitory computer readable medium of claim 31, wherein the step of generating a patient-specific anatomical model of a heart from medical image data of a patient comprises:
  detecting a patient-specific left ventricle endocardium model, a patient-specific right ventricle endocardium model, and a patient-specific epicardium model in the medical image data; and
  fusing the left ventricle endocardium model, the right ventricle endocardium model and the epicardium model into a single bi-ventricular volumetric mesh.

33. The non-transitory computer readable medium of claim 32, wherein the step of generating a patient-specific anatomical model of a heart from medical image data of a patient further comprises:
  mapping spatial information corresponding to at least one of scars, grey zones, or fibrosis identified from medical-image data and other clinical measurements onto the bi-ventricular volumetric mesh.

34. The non-transitory computer readable medium of claim 32, wherein the step of generating a patient-specific anatomical model of a heart from medical image data of a patient further comprises:
  registering a tensor field of an in-vivo diffusion tensor magnetic resonance image of cardiac fibers to the bi-ventricular volumetric mesh.

35. The non-transitory computer readable medium of claim 32, wherein the step of generating a patient-specific anatomical model of a heart from medical image data of a patient further comprises:
  generating a global model of fiber architecture based on the bi-ventricular volumetric mesh and nominal values for fiber elevation angle distribution.

36. The non-transitory computer readable medium of claim 31, wherein the step of computing the transmembrane action potential on at least one node of the level-set representation of the patient-specific anatomical model of the heart further comprising:
  solving at least one monodomain electrophysiology model using a Lattice-Boltzmann method on at least one node of the level-set representation on a Cartesian grid.

37. The non-transitory computer readable medium of claim 31, wherein the step of generating a level-set representation of the patient-specific anatomical model of the heart on a Cartesian grid comprises:
  discretizing a domain of the patient-specific model of the heart using a Cartesian lattice in which each node is connected via edges to a predetermined number of neighboring nodes.

38. The non-transitory computer readable medium of claim 31, wherein the step of computing the transmembrane action potential on at least one node of the level-set representation of the patient-specific anatomical model of the heart further comprises:
  at each of a plurality of time steps:
    for at least one node of the level-set representation of the patient-specific anatomical model of the heart on a Cartesian grid,
    calculating collisions of particles for each edge connected to the node based on a distribution function calculated for each edge;
    calculating the transmembrane action potential at the node based on the collisions of particles calculated at the node;
    updating all cellular model-dependent internal variables at the node;
    updating the distribution function for each edge of the node to represent streaming of a particle traveling along each of the edges to a neighboring node; and
    applying optional Dirichlet boundary conditions.

39. The non-transitory computer readable medium of claim 38, wherein the step of calculating collisions of particles for each edge connected to the node based on a distribution function calculated for each edge comprises:
  calculating collisions on each edge connected to the node as:
  $f_i = f_i - A_{ij}(f_j - \omega_j \upsilon) + \Delta t \omega_i R(\upsilon, \{h\})$
  where $f_i$ is the distribution function that represents a probability of finding a particle traveling along the $i^{th}$ edge $e_i$ connected to the node, $A=(A_{ij})_{i,j} \in$ is a collision matrix that relaxes the distribution function $f_i$ towards a local potential value, $\upsilon$, $R(\upsilon, \{h\})$ is a model-dependent term for electrophysiological currents, which depends on a model-dependent set of internal variables {h}, and $\omega_i$ and $\omega_j$ are weighting factors for edges $e_i$ and $e_j$, respectively.

40. The non-transitory computer readable medium of claim 39, wherein the collision matrix A is defined as $A=M^{-1}SM$,
where M is a matrix designed to transform the distribution functions into a vector of moments and $S^{-1}$ is a matrix of relaxation times corresponding to the moments, and M and $S^{-1}$ are respectively defined as:

$$M = \begin{pmatrix} 1 & 1 & 1 & 1 & 1 & 1 & 1 \\ 0 & -1 & 0 & 0 & 0 & 0 & 0 \\ 0 & 0 & 1 & -1 & 0 & 0 & 0 \\ 0 & 0 & 0 & 0 & 1 & -1 & 0 \\ 1 & 1 & 1 & 1 & 1 & 1 & -6 \\ 1 & 1 & -1 & -1 & 0 & 0 & 0 \\ 1 & 1 & 1 & 1 & -2 & -2 & 0 \end{pmatrix}$$

$$S^{-1} = \begin{pmatrix} \tau_1 & 0 & 0 & 0 & 0 & 0 & 0 \\ 0 & \tau_{22} & \tau_{23} & \tau_{24} & 0 & 0 & 0 \\ 0 & \tau_{32} & \tau_{33} & \tau_{34} & 0 & 0 & 0 \\ 0 & \tau_{42} & \tau_{43} & \tau_{44} & 0 & 0 & 0 \\ 0 & 0 & 0 & 0 & \tau_5 & 0 & 0 \\ 0 & 0 & 0 & 0 & 0 & \tau_6 & 0 \\ 0 & 0 & 0 & 0 & 0 & 0 & \tau_7 \end{pmatrix}.$$

41. The non-transitory computer readable medium of claim 38, wherein the step of calculating the transmembrane action potential at the node based on the collisions of particles calculated at the node comprises:

calculating the transmembrane action potential for a node x as:

$\upsilon(x,t)=\Sigma_i f_i(x,t)$ where $f_i(x, t)$ represents a probability of finding a particle traveling along the $i^{th}$ edge $e_i$ connected to node x at time step t.

42. The non-transitory computer readable medium of claim 38, wherein the step of updating all cellular model-dependent internal variables at the node comprises:

using an integration scheme to solve a system of model-specific differential-algebraic equations modeling each internal variables.

43. The non-transitory computer readable medium of claim 38, wherein the step of updating the distribution function for each edge of the node to represent streaming of a particle traveling along each of the edges to a neighboring node comprises:

calculating the distribution functions at the next time step as:

$f_i(x+e_i\Delta t,t+\Delta t)=f_i(x,t)$ where $f_i(x,t)$ represents a probability of finding a particle traveling along the $i^{th}$ edge $e_i$ connected to node x at time step t.

44. The non-transitory computer readable medium of claim 31, wherein the step of identifying key electrophysiology structures of interest from the patient-specific anatomical model and medical image data comprises:

identifying and tagging surface zones representing electrophysiology structures of the heart using machine learning algorithms; and assigning spatially variable electrophysiological properties of myocardial tissue.

45. The non-transitory computer readable medium of claim 44, wherein the step of assigning spatially variable properties of the myocardial tissue comprises:

assigning tissue electrical conductivity and other model-dependent internal parameters estimated from medical image data and other clinical measurements.

\* \* \* \* \*